(12) United States Patent
Thorens et al.

(10) Patent No.: US 11,406,772 B2
(45) Date of Patent: Aug. 9, 2022

(54) AEROSOL GENERATING SYSTEM WITH PREVENTION OF CONDENSATE LEAKAGE

(71) Applicant: Philip Morris Products S.A., Neuchatel (CH)

(72) Inventors: Michel Thorens, Moudon (CH); Jean-Marc Flick, Pomy (CH); Olivier Yves Cochand, Dombresson (CH); Flavien Dubief, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 528 days.

(21) Appl. No.: 16/132,635

(22) Filed: Sep. 17, 2018

(65) Prior Publication Data

US 2019/0014826 A1    Jan. 17, 2019

Related U.S. Application Data

(62) Division of application No. 13/990,067, filed as application No. PCT/EP2011/006055 on Dec. 2, 2011, now Pat. No. 10,104,911.

(30) Foreign Application Priority Data

Dec. 3, 2010  (EP) .................... 10252048

(51) Int. Cl.
*A61M 11/04* (2006.01)
*A61M 15/06* (2006.01)
(Continued)

(52) U.S. Cl.
CPC .......... *A61M 11/042* (2014.02); *A24F 40/40* (2020.01); *A24F 40/485* (2020.01); *A61M 15/06* (2013.01);
(Continued)

(58) Field of Classification Search
CPC ..... A24B 15/165; A24B 15/18; A24F 47/008; A24F 47/002; A61M 16/108;
(Continued)

(56) References Cited

U.S. PATENT DOCUMENTS 4,275,747 A    6/1981 Miller
4,419,302 A   12/1983 Nishino et al.
(Continued)

FOREIGN PATENT DOCUMENTS

CA    2 641 869 A1    5/2010
CA       2641869 A1 *  5/2010  ........... A24F 47/008
(Continued)

OTHER PUBLICATIONS

Korean Office Action dated Aug. 6, 2019, in Patent Application No. 10-2019-7021868, citing document AA therein, 12 pages (with English translation).
(Continued)

*Primary Examiner* — Elliot S Ruddie
(74) *Attorney, Agent, or Firm* — Oblon, McClelland, Maier & Neustadt, L.L.P.

(57) ABSTRACT

There is provided an aerosol generating system for heating a liquid aerosol-forming substrate. The system includes an aerosol-forming chamber, and a leakage preventer for preventing or reducing leakage of liquid aerosol condensate from the aerosol generating system. The leakage preventer may include one or more of: at least one cavity in a wall of the aerosol-forming chamber, for collecting droplets of condensed liquid aerosol-forming substrate; at least one hooked member for collecting droplets of condensed liquid aerosol-forming substrate; an impactor for disrupting airflow in the aerosol-forming chamber so as to collect liquid
(Continued)

droplets; and a closure member for substantially sealing the aerosol-forming chamber when the aerosol generating system is not in use.

7 Claims, 3 Drawing Sheets

(51) Int. Cl.

| | |
|---|---|
| *A61M 16/10* | (2006.01) |
| *A61M 16/20* | (2006.01) |
| *A24F 40/40* | (2020.01) |
| *A24F 40/485* | (2020.01) |
| *A61M 16/08* | (2006.01) |
| *A61M 16/00* | (2006.01) |
| *A24F 40/10* | (2020.01) |

(52) U.S. Cl.
CPC ........ *A61M 16/108* (2014.02); *A61M 16/202* (2014.02); *A24F 40/10* (2020.01); *A61M 16/0808* (2013.01); *A61M 2016/0024* (2013.01); *A61M 2205/3646* (2013.01)

(58) Field of Classification Search
CPC .. A61M 16/202; A61M 11/041; A61M 15/06; A61M 16/0808; A61M 2016/0024; A61M 2205/3646; B05B 17/00–085
USPC ......... 128/202.21; 131/194, 198.2, 270, 273, 131/290, 329, 330, 360; 290/1 R
See application file for complete search history.

(56) References Cited

U.S. PATENT DOCUMENTS

| | | | | |
|---|---|---|---|---|
| 4,846,199 | A | 7/1989 | Rose | |
| 5,935,975 | A | 8/1999 | Rose | |
| 7,832,410 | B2 | 11/2010 | Hon | |
| 2005/0103891 | A1* | 5/2005 | Abergel ................ | F16K 15/028 239/333 |
| 2007/0267031 | A1 | 11/2007 | Hon | |
| 2008/0230052 | A1* | 9/2008 | Montaser .......... | A61M 15/0085 128/200.16 |
| 2009/0272379 | A1 | 11/2009 | Thorens et al. | |
| 2010/0200008 | A1 | 8/2010 | Taieb | |
| 2011/0120455 | A1* | 5/2011 | Murphy ............. | A61M 15/009 128/200.18 |

FOREIGN PATENT DOCUMENTS

| | | | |
|---|---|---|---|
| CN | 87 1 05919 | A | 9/1988 |
| CN | 201079011 | Y | 7/2008 |
| CN | 201104488 | Y | 8/2008 |
| CN | 201238610 | Y | 5/2009 |
| CN | 201479921 | U | 5/2010 |
| EA | 200802045 | A1 | 2/2009 |
| FR | 2128256 | | 10/1972 |
| JP | 2000-510763 | | 8/2000 |
| JP | 2007-532118 | A | 11/2007 |
| JP | 2009-526540 | | 7/2009 |
| KR | 10-0443821 | B1 | 10/2004 |
| KR | 20-2009-0003871 | A | 4/2009 |
| KR | 10-2009-0091809 | A | 8/2009 |
| WO | WO 97/42993 | A2 | 11/1997 |
| WO | 01/39619 | A1 | 6/2001 |
| WO | WO 2007/093757 | A1 | 8/2007 |
| WO | WO 2007/131449 | A1 | 11/2007 |
| WO | 2009132793 | | 11/2009 |

OTHER PUBLICATIONS

Office Action dated Aug. 31, 2015 in Japanese Patent Application No. 2013-541250 (with English language translation).
Office Action dated Sep. 10, 2015 in Eurasian Patent Application No. 201390819/31 (with English language translation).
Combined Chinese Office Action and Search Report dated Nov. 4, 2014 in Patent Application No. 201180058140.9 (with English Translation).
Combined Chinese Office Action and Search Report dated Jan. 4, 2016 in Patent Application No. 201180058140.9 (with English Translation).
Korean Office Action with English translation dated Feb. 9, 2018 in corresponding Korean Patent Application No. 10-2013-7013271, citing documents AB, BO, and BP therein (13 pages).
Office Action dated Mar. 18, 2016 in Eurasian Patent Application No. 201390819 (with English language translation).
Office Action dated Aug. 13, 2014 in Colombian Patent Application No. 13-156667-3 (with English language translation).
International Search Report and Written Opinion dated Mar. 8, 2012 in International Application No. PCT/EP2011/006055.
Office Action dated Apr. 9, 2021 in corresponding Korean Patent Application No. 10-2020-7024573 (with English Translation), citing documents AO and AP therein, 9 pages.

* cited by examiner

AEROSOL GENERATING SYSTEM WITH PREVENTION OF CONDENSATE LEAKAGE

CROSS-REFERENCE TO RELATED APPLICATIONS

This application is a divisional application of and claims the benefit of priority under 35 U.S.C. § 120 to U.S. application Ser. No. 13/990,067, filed on Aug. 9, 2013, which is a U.S. National Stage application of PCT/EP2011/006055, filed on Dec. 2, 2011, and claims benefit of priority under 35 U.S.C. § 119 to EP 10252048.3, filed on Dec. 3, 2010, the entire contents of each of which are incorporated herein by reference.

The present invention relates to an aerosol generating system. In particular, the present invention relates to an aerosol generating system in which the aerosol-forming substrate is liquid.

WO-A-2009/132793 discloses an electrically heated smoking system. A liquid is stored in a liquid storage portion, and a capillary wick has a first end which extends into the liquid storage portion for contact with the liquid therein, and a second end which extends out of the liquid storage portion. A heating element heats the second end of the capillary wick. The heating element is in the form of a spirally wound electric heating element in electrical connection with a power supply, and surrounding the second end of the capillary wick. In use, the heating element may be activated by the user to switch on the power supply. Suction on a mouthpiece by the user causes air to be drawn into the electrically heated smoking system over the capillary wick and heating element and subsequently into the mouth of the user.

The aerosol generating systems of the prior art, including the electrically operated smoking system referred to above, do have a number of advantages, but there is still opportunity for improvement in the design.

According to a first aspect of the invention, there is provided an aerosol generating system for heating a liquid aerosol-forming substrate, the system comprising: an aerosol-forming chamber; and leakage prevention means configured to prevent or reduce leakage of liquid aerosol condensate from the aerosol generating system.

The aerosol generating system is arranged to vaporize the liquid aerosol-forming substrate to form a vapour, which condenses in the aerosol-forming chamber to form the aerosol. Thus, the aerosol-forming chamber simply assists or facilitates the generation of the aerosol. The aerosol generating system may include the aerosol-forming substrate or may be adapted to receive the aerosol-forming substrate. As known to those skilled in the art, an aerosol is a suspension of solid particles or liquid droplets in a gas, such as air.

An advantage of the invention is that leakage of liquid aerosol condensate from the aerosol generating system is prevented or at least substantially reduced. The condensed liquid (liquid condensate) may form due to a change in temperature, for example a sudden temperature drop. Alternatively or additionally, the liquid condensate may accumulate in cavities, grooves, corners or other portions of the aerosol generating system where there is reduced airflow. The rate of condensation is affected by the vapour pressure of the aerosol-forming substrate, the temperature gradient between the vapour and the housing or wall of the aerosol generating system, and other factors, for example the airflow and turbulence. Minimising, or preferably preventing, leakage of the liquid aerosol condensate is important to avoid wastage of the liquid aerosol-forming substrate. In addition, if liquid leaks out of the aerosol generating system, this may cause inconvenience for the user. For example, the aerosol generating system may become wet or sticky.

The liquid aerosol-forming substrate preferably has physical properties, for example boiling point and vapour pressure, suitable for use in the aerosol generating system. If the boiling point is too high, it may not be possible to vaporize the liquid but, if the boiling point is too low, the liquid may vaporize too readily. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts, nicotine solutions and natural or artificial flavours. Preferably, the liquid further comprises an aerosol former. Examples of suitable aerosol formers are glycerine and propylene glycol.

In a first embodiment of the invention, the leakage prevention means comprises at least one cavity in a wall of the aerosol-forming chamber, for collecting liquid condensate formed from the aerosol-forming substrate.

Providing at least one cavity in a wall of the aerosol-forming chamber allows condensed droplets of the liquid to be collected. Preferably, the at least one cavity interrupts the flow route for droplets of condensed liquid which may otherwise leak out of the aerosol generating system. Thus, leakage of condensed liquid from the aerosol generating system is prevented or at least reduced. The at least one cavity may have any suitable size and shape and may be located at any suitable location in the aerosol-forming chamber. Preferably, the at least one cavity is close to an outlet end of the aerosol generating system. If the aerosol generating system includes a liquid storage portion or a capillary wick or both a liquid storage portion and a capillary wick, the at least one cavity may comprise a return path for returning condensed liquid droplets to the liquid storage portion or capillary wick.

In the first embodiment of the invention, the at least one cavity may contain capillary material. Providing capillary material in the at least one cavity minimises the free liquid. This reduces the likelihood that condensed liquid will leak from the aerosol generating system. The capillary material may comprise any suitable material or combination of materials which is able to retain the collected liquid. The particular preferred material or materials will depend on the physical properties of the liquid aerosol-forming substrate. Examples of suitable materials are a sponge or foam material, ceramic- or graphite-based materials in the form of fibres or sintered powders, a foamed metal or plastics material, a fibrous material, for example made of spinned or extruded fibres, such as cellulose acetate, polyester, or bonded polyolefin, polyethylene, terylene or polypropylene fibres, nylon fibres or ceramic. Most preferably, the capillary material substantially fills the cavities so as to minimise the free liquid.

If the aerosol generating system includes a liquid storage portion or a capillary wick or both a liquid storage portion and a capillary wick, the capillary material may provide a return path for returning condensed liquid droplets to the liquid storage portion or capillary wick. The capillary material may be in contact with the capillary wick. The capillary material in the at least one cavity and the capillary wick may comprise the same material or different materials.

In a second embodiment of the invention, the leakage prevention means comprises at least one hooked member for collecting droplets of liquid condensate formed from the aerosol-forming substrate.

Providing a hooked member allows condensed droplets of the liquid aerosol-forming substrate to be collected. Preferably, the at least one hooked member interrupts the flow route for droplets of condensed liquid. Thus, leakage of liquid condensate from the aerosol generating system is prevented. The at least one hooked member may have any suitable size and shape and may be located at any suitable location. For example, the hooked member may be positioned on a wall of the aerosol-forming chamber.

In the second embodiment of the invention, the at least one hooked member may comprise a recycle path for recycling the collected droplets of the liquid condensate. The recycle path may comprise an angled portion of the hooked member. If the aerosol generating system includes a liquid storage portion or a capillary wick or both a liquid storage portion and a capillary wick, the recycle path may return condensed liquid droplets to the liquid storage portion or capillary wick. The trapping and transportation of condensate droplets can be enhanced by surface properties (for example, but not limited to, surface profile, surface roughness) or material (for example, but not limited to, use of a hydrophobic or hydrophilic material) of an inner wall of the aerosol generating system, for example the inner wall of the aerosol-forming chamber.

In the second embodiment of the invention, the at least one hooked member includes capillary material. The capillary material may be provided on part or all of the collecting surface of the hooked member. Providing capillary material on the at least one hooked member minimises the free liquid. This reduces the likelihood that condensed liquid will leak from the aerosol generating system. The capillary material may comprise any suitable material or combination of materials which is able to retain the collected liquid. The particular preferred material or materials will depend on the physical properties of the liquid aerosol-forming substrate. Examples of suitable materials are a sponge or foam material, ceramic- or graphite-based materials in the form of fibres or sintered powders, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

If the hooked member includes a recycle path, preferably, the recycle path includes the capillary material. This improves recycling of the condensed liquid droplets. If the aerosol generating system includes a liquid storage portion or a capillary wick or both a liquid storage portion and a capillary wick, the capillary material may return condensed liquid droplets to the liquid storage portion or capillary wick. The capillary material may be in contact with the capillary wick. The capillary material on the at least one hooked member and the capillary wick may comprise the same material or different materials.

In a third embodiment of the invention, the leakage prevention means comprises an impactor for disrupting airflow in the aerosol-forming chamber so as to collect droplets of liquid being formed from the aerosol-forming substrate.

Providing an impactor which disrupts the airflow allows droplets of the liquid aerosol-forming substrate to be collected. This is because, as the airflow is disrupted, some liquid droplets cannot be carried in the airflow and impact on the impactor instead. The collected liquid droplets tend to be the larger liquid droplets. The collected liquid droplets cannot leak out of the aerosol generating system. Thus, leakage of liquid condensate from the aerosol generating system is prevented. The impactor may have any suitable size and shape and may be located at any point downstream of the vapour formation.

In the third embodiment of the invention, the impactor may include capillary material. The capillary material is preferably provided on part or all of the upstream surface of the impactor. The capillary material may be provided on other surfaces of the impactor. Providing capillary material on the collecting surface of the impactor minimises the free liquid. This reduces the likelihood that liquid condensate will leak from the aerosol generating system. The capillary material may comprise any suitable material or combination of materials which is able to retain the collected liquid. The particular preferred material or materials will depend on the physical properties of the liquid aerosol-forming substrate. Examples of suitable materials are a sponge or foam material, ceramic- or graphite-based materials in the form of fibres or sintered powders, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

If the aerosol generating system includes a liquid storage portion or a capillary wick or both a liquid storage portion and a capillary wick, the capillary material on the impactor may return liquid droplets to the liquid storage portion or capillary wick. The capillary material on the impactor may be in contact with the capillary wick. The capillary material on the impactor and the capillary wick may comprise the same material or different materials.

In a fourth embodiment of the invention, the leakage prevention means comprises a closure member for substantially sealing the aerosol-forming chamber when the aerosol generating system is not in use.

Providing a closure member which substantially seals the aerosol-forming chamber when the aerosol generating system is not in use substantially prevents any condensed liquid droplets from leaking out of the aerosol generating system when it is not in use. It should be understood that the closure member need only substantially seal the exit of the aerosol-forming chamber. The inlet of the aerosol-forming chamber may remain open, even when the closure member is in the closed position.

The closure member may have any suitable size and shape. The closure member may be manually operable by a user. Alternatively, the closure member may be electrically operable, either on user instruction or automatically.

The closure member may include capillary material. The capillary material may be provided on part or all of the upstream surface of the closure member. The capillary material will retain any liquid which collects on the closure member. This reduces the likelihood that condensed liquid will leak from the aerosol generating system. The capillary material may comprise any suitable material or combination of materials which is able to retain the collected liquid. The particular preferred material or materials will depend on the physical properties of the liquid aerosol-forming substrate. Examples of suitable materials are a sponge or foam material, ceramic- or graphite-based materials in the form of fibres or sintered powders, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

If the aerosol generating system includes a liquid storage portion or a capillary wick or both a liquid storage portion and a capillary wick, the capillary material on the closure member may return liquid droplets to the liquid storage portion or capillary wick. The capillary material on the closure member may be in contact with the capillary wick when the aerosol generating system is not in use. The capillary material on the closure member and the capillary wick may comprise the same material or different materials.

The aerosol generating system may further comprise a liquid storage portion for storing the liquid aerosol-forming substrate.

An advantage of providing a liquid storage portion is that the liquid in the liquid storage portion is protected from ambient air (because air cannot generally enter the liquid storage portion) and, in some embodiments light, so that the risk of degradation of the liquid is significantly reduced. Moreover, a high level of hygiene can be maintained. The liquid storage portion may not be refillable. Thus, when the liquid in the liquid storage portion has been used up, the aerosol generating system is replaced. Alternatively, the liquid storage portion may be refillable. In that case, the aerosol generating system may be replaced after a certain number of refills of the liquid storage portion. Preferably, the liquid storage portion is arranged to hold liquid for a pre-determined number of puffs.

The aerosol generating system may further comprise a capillary wick for conveying the liquid aerosol-forming substrate by capillary action.

Preferably, the capillary wick is arranged to be in contact with liquid in the liquid storage portion. Preferably, the capillary wick extends into the liquid storage portion. In that case, in use, liquid is transferred from the liquid storage portion by capillary action in the capillary wick. In one embodiment, liquid in one end of the capillary wick is vaporized to form a supersaturated vapour. The supersaturated vapour is mixed with and carried in the air flow. During the flow, the vapour condenses to form the aerosol and the aerosol is carried towards the mouth of a user. The liquid aerosol-forming substrate has physical properties, including surface tension and viscosity, which allow the liquid to be transported through the capillary wick by capillary action.

The capillary wick may have a fibrous or spongy structure. The capillary wick preferably comprises a bundle of capillaries. For example, the capillary wick may comprise a plurality of fibres or threads or other fine bore tubes. The fibres or threads may be generally aligned in the longitudinal direction of the aerosol generating system. Alternatively, the capillary wick may comprise sponge-like or foam-like material formed into a rod shape. The rod shape may extend along the longitudinal direction of the aerosol generating system. The structure of the wick forms a plurality of small bores or tubes, through which the liquid can be transported by capillary action. The capillary wick may comprise any suitable material or combination of materials. Examples of suitable materials are capillary materials, for example a sponge or foam material, ceramic- or graphite-based materials in the form of fibres or sintered powders, foamed metal or plastics material, a fibrous material, for example made of spinned or extruded fibres, such as cellulose acetate, polyester, or bonded polyolefin, polyethylene, terylene or polypropylene fibres, nylon fibres or ceramic. The capillary wick may have any suitable capillarity and porosity so as to be used with different liquid physical properties. The liquid has physical properties, including but not limited to viscosity, surface tension, density, thermal conductivity, boiling point and vapour pressure, which allow the liquid to be transported through the capillary device by capillary action.

The aerosol generating system may be electrically operated. The electrically operated aerosol generating system may further comprise an electric heater for heating the liquid aerosol-forming substrate.

The electric heater may comprise a single heating element. Alternatively, the electric heater may comprise more than one heating element for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source or an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. The liquid storage portion may incorporate a disposable heating element. Alternatively, one or more heating needles or rods that run through the liquid aerosol-forming substrate may also be suitable. Alternatively, the at least one electric heating element may be a disk (end) heater or a combination of a disk heater with heating needles or rods. Alternatively, the at least one electric heating element may comprise a flexible sheet of material. Other alternatives include a heating wire or filament, for example a Ni—Cr, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to heat the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the liquid aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the substrate. Alternatively, the heat from the heating element may be conducted to the substrate by means of a heat conductive element.

Alternatively, the at least one heating element may transfer heat to the incoming ambient air that is drawn through the aerosol generating system during use, which in turn heats the aerosol-forming substrate by convection. The ambient air may be heated before passing through the aerosol-forming substrate. Alternatively, the ambient air may be first drawn through the liquid substrate and then heated.

In one preferred embodiment, the aerosol generating system comprises an electric heater, a capillary wick and a liquid storage portion. In that embodiment, preferably the capillary wick is arranged to be in contact with liquid in the liquid storage portion. In use, liquid is transferred from the liquid storage portion towards the electric heater by capillary action in the capillary wick. In one embodiment, the capillary wick has a first end and a second end, the first end extending into the liquid storage portion for contact with liquid therein and the electric heater being arranged to heat liquid in the second end. When the heater is activated, the liquid at the second end of the capillary wick is vaporized by the heater to form the supersaturated vapour. The supersaturated vapour is mixed with and carried in the air flow. During the flow, the vapour condenses to form the aerosol and the aerosol is carried towards the mouth of a user.

As discussed above, the capillary wick may comprise any suitable material. The capillary properties of the wick, combined with the properties of the liquid, ensure that the wick is always wet in the heating area. If the wick is dry, there may be overheating, which can lead to thermal degradation of liquid.

The capillary wick and the heater, and optionally the liquid storage portion, may be removable from the aerosol generating system as a single component.

The aerosol generating system may comprise at least one air inlet. The aerosol generating system may comprise at least one air outlet. The aerosol-forming chamber is located between the air inlet and air outlet so as to define an air flow route from the air inlet to the air outlet via the aerosol-forming chamber, so as to convey the aerosol to the air outlet and into the mouth of a user.

The aerosol generating system may be electrically operated and may further comprise an electric power supply. The aerosol generating system may further comprise electric circuitry. In one embodiment, the electric circuitry comprises a sensor to detect air flow indicative of a user taking a puff. In that case, preferably, the electric circuitry is arranged to provide an electric current pulse to the electric heater when the sensor senses a user taking a puff. Preferably, the time-period of the electric current pulse is pre-set, depending on the amount of liquid desired to be vaporized. The electric circuitry is preferably programmable for this purpose. Alternatively, the electric circuitry may comprise a manually operable switch for a user to initiate a puff. The time-period of the electric current pulse is preferably pre-set depending on the amount of liquid desired to be vaporized. The electric circuitry is preferably programmable for this purpose.

Preferably, the aerosol generating system comprises a housing. Preferably, the housing is elongate. If the aerosol generating includes a capillary wick, the longitudinal axis of the capillary wick and the longitudinal axis of the housing may be substantially parallel. The housing may comprise a shell and a mouthpiece. In that case, all the components may be contained in either the shell or the mouthpiece. In one embodiment, the housing includes a removable insert comprising the liquid storage portion, the capillary wick and the heater. In that embodiment, those parts of the aerosol generating system may be removable from the housing as a single component. This may be useful for refilling or replacing the liquid storage portion, for example.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the aerosol generating system is portable. The aerosol generating system may be a smoking system and may have a size comparable to a conventional cigar or cigarette. The smoking system may have a total length between approximately 30 mm and approximately 150 mm. The smoking system may have an external diameter between approximately 5 mm and approximately 30 mm.

Preferably, the aerosol generating system is an electrically operated smoking system.

Features described in relation to one aspect of the invention may be applicable to another aspect of the invention.

The invention will be further described, by way of example only, with reference to the accompanying drawings, of which:

Figure 1:
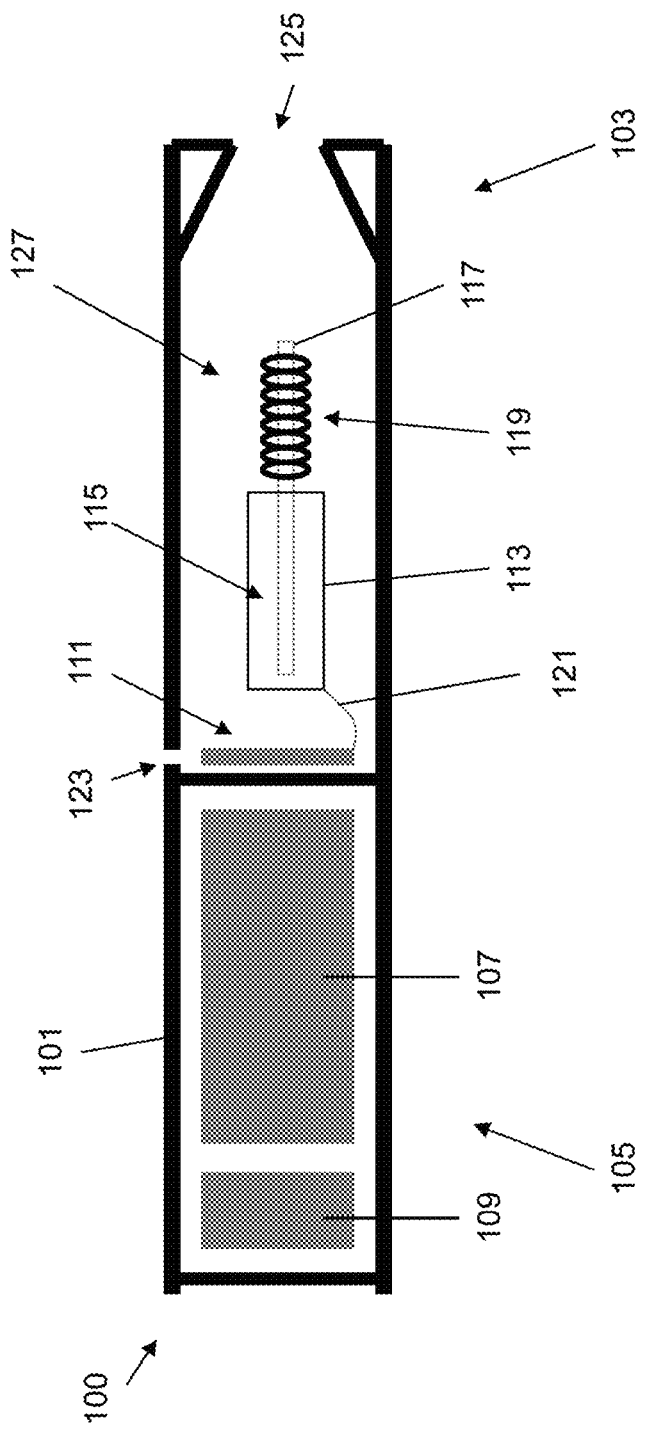
FIG. 1 shows one example of an aerosol generating system having a liquid storage portion.

FIG. 1 shows one example of an aerosol generating system having a liquid storage portion. In FIG. 1, the system is an electrically operated smoking system. The smoking system 100 of FIG. 1 comprises a housing 101 having a first end which is the mouthpiece end 103 and a second end which is the body end 105. In the body end, there is provided an electric power supply in the form of battery 107 and electric circuitry in the form of hardware 109 and puff detection system 111. In the mouthpiece end, there is provided a liquid storage portion in the form of cartridge 113 containing liquid 115, a capillary wick 117 and a heater 119. Note that the heater is only shown schematically in FIG. 1. In the exemplary embodiment shown in FIG. 1, one end of capillary wick 117 extends into cartridge 113 and the other end of capillary wick 117 is surrounded by the heater 119. The heater is connected to the electric circuitry via connections 121, which may pass along the outside of cartridge 113 (not shown in FIG. 1). The housing 101 also includes an air inlet 123, an air outlet 125 at the mouthpiece end, and an aerosol-forming chamber 127.

In use, operation is as follows. Liquid 115 is conveyed by capillary action from the cartridge 113 from the end of the wick 117 which extends into the cartridge to the other end of the wick which is surrounded by heater 119. When a user draws on the aerosol generating system at the air outlet 125, ambient air is drawn through air inlet 123. In the arrangement shown in FIG. 1, the puff detection system 111 senses the puff and activates the heater 119. The battery 107 supplies electrical energy to the heater 119 to heat the end of the wick 117 surrounded by the heater. The liquid in that end of the wick 117 is vaporized by the heater 119 to create a supersaturated vapour. At the same time, the liquid being vaporized is replaced by further liquid moving along the wick 117 by capillary action. (This is sometimes referred to as "pumping action".) The supersaturated vapour created is mixed with and carried in the air flow from the air inlet 123. In the aerosol-forming chamber 127, the vapour condenses to form an inhalable aerosol, which is carried towards the outlet 125 and into the mouth of the user.

In the embodiment shown in FIG. 1, the hardware 109 and puff detection system 111 are preferably programmable. The hardware 109 and puff detection system 111 can be used to manage the aerosol generating system operation.

FIG. 1 shows one example of an aerosol generating system according to the present invention. Many other examples are possible, however. The aerosol generating system simply needs to include leakage prevention means (to be described below with reference to FIGS. 2 to 9) configured to prevent or reduce leakage of liquid aerosol condensate from the aerosol generating system. For example, the system need not be electrically operated. For example, the system need not be a smoking system. In addition, the system may not include a heater, in which case another device may be included to vaporize the liquid aerosol-forming substrate. For example, a puff detection system need not be provided. Instead, the system could operate by manual activation, for example the user operating a switch when a puff is taken. For example, the overall shape and size of the housing could be altered. Moreover, the system may not include a capillary wick. In that case, the system may include another mechanism for delivering liquid for vaporization.

However, in a preferred embodiment, the system does include a liquid storage portion and a capillary wick for conveying the liquid from the liquid storage portion. The capillary wick can be made from a variety of porous or capillary materials and preferably has a known, pre-defined capillarity. Examples include ceramic- or graphite-based materials in the form of fibres or sintered powders. Wicks of different porosities can be used to accommodate different liquid physical properties such as viscosity and surface tension. The wick must be suitable so that the required amount of liquid can be delivered to the heater.

As discussed above, according to the invention, the aerosol generating system includes leakage prevention means configured to prevent or reduce leakage of condensed liquid from the aerosol generating system. A number of embodiments of the invention, including the leakage prevention means, will now be described with reference to FIGS. 2 to 9. The embodiments are based on the example shown in FIG. 1, although are applicable to other embodiments of aerosol generating systems. Note that FIG. 1 and the following FIGS. 2 to 9 are schematic in nature. In particular, the components shown are not to scale either individually or relative to one another.

Figure 2:
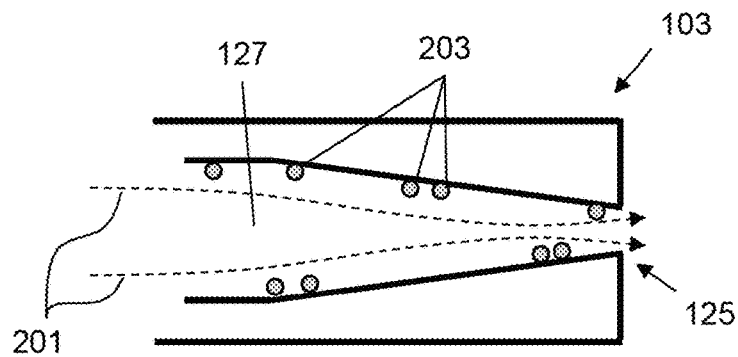
FIG. 2 shows an enlarged view of the mouthpiece end of an aerosol generating system similar to that shown in FIG. 1.

FIG. 2 shows an enlarged view of the mouthpiece end of an aerosol generating system similar to that of FIG. 1. FIG. 2 only shows the mouthpiece end 103 including the aerosol-forming chamber 127 and the air outlet 125. Other components are not shown in FIG. 2 for clarity.

In FIG. 2, the air flow is shown schematically by arrows 201. It can be seen that liquid droplets (shown schematically at 203) tend to condense on the inside walls of the aerosol-forming chamber 127, particularly towards the air outlet 125. Such liquid droplets may be formed as the vapour condenses to form the aerosol. If the airflow does not carry all the droplets out of the outlet 125 and into the mouth of the user, droplets, particularly the larger droplets, may accumulate on the inside walls of the aerosol-forming chamber 127, as shown in FIG. 2. The condensate droplets 203 may run out of the outlet 125, causing the aerosol generating system to become wet or sticky. This will inconvenience the user.

Figures 3, 4:
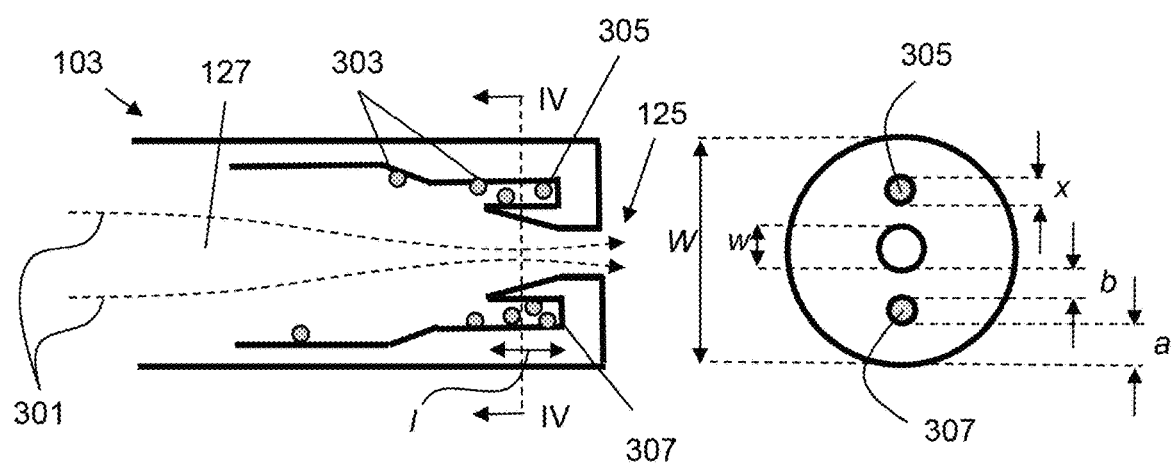
FIG. 3 shows an enlarged view of the mouthpiece end of an aerosol generating system according to a first embodiment of the invention.
FIG. 4 is a cross sectional view along line IV-IV of FIG. 3.

FIG. 3 shows an enlarged view of the mouthpiece end of an aerosol generating system according to a first embodiment of the invention. FIG. 4 is a cross sectional view along line IV-IV of FIG. 3. FIG. 3 shows the mouthpiece end 103 including the aerosol-forming chamber 127 and the air outlet 125. Other components are not shown in FIG. 3, for clarity. In FIG. 3, the air flow is shown schematically by arrows 301 and liquid droplets 303 are shown accumulating on the inside walls of the aerosol-forming chamber 127.

In the embodiment shown in FIGS. 3 and 4, the inside walls of the aerosol-forming chamber 127 are provided with droplet collecting cavities or recesses 305, 307. The two cavities 305, 307 are provided on opposite sides of the air outlet 125. In the embodiment shown in FIGS. 3 and 4, upper cavity 305 is in the form of a substantially cylindrical cavity. As seen in FIG. 4, the cavity 305 has a substantially circular cross section. The cavity 305 is a blind hole. That is to say, the cavity 305 does not extend to the outside of the aerosol generating system. Similarly, in the embodiment shown in FIGS. 3 and 4, lower cavity 307 is also in the form of a substantially cylindrical cavity with a substantially circular cross section. The cavity 307 is also a blind hole, not extending to the outside of the aerosol generating system.

The cavities 305, 307 act as leakage prevention means. They collect liquid condensate droplets 303 which have accumulated on the inside walls of the aerosol-forming chamber 127. The cavities 305, 307 are positioned so as to interrupt the flow route for liquid droplets 303 running towards the air outlet. Thus, the liquid droplets are prevented from leaking out of the air outlet of the aerosol generating system.

In FIGS. 3 and 4, the cavities are substantially cylindrical with a substantially circular cross section. However, the cavities may have any suitable cross section and shape. The cavities may have any suitable diameter. In FIGS. 3 and 4, the cross sectional dimension of the aerosol generating system at the air outlet end is shown as W and the cross sectional dimension of the air outlet itself is shown as w. W and w may have any suitable values. For example, W may be between 5 mm and 30 mm which is the typical range of diameters of cigarettes and cigars. The cross sectional width w of the air outlet may be determined by several factors. If w is relatively small (for example, 1 to 2 mm), the aerosol passing through the air outlet is concentrated (that is to say, has an increased density) so that condensation may be increased. This may increase the droplet or particle size of the aerosol. In addition, a relatively small w increases the resistance to draw (RTD) and may cause increased turbulence of the airflow in the housing. This will also affect the aerosol particle size. On the other hand, a relatively large cross sectional width w increases the diffusion angle of the aerosol. This may also affect the aerosol properties. However, a relatively large w may also help to prevent leakage of condensation. The cross sectional widths w and W may be varied in proportion to one another. For example, a small W with a relatively large w or a large W with a relatively small w, may affect the aerosol properties. Preferably, the cross sectional width w of the air outlet is between 1 mm and 5 mm.

In FIGS. 3 and 4, the cavities 305, 307 are shown with a cross sectional dimension x. Dimension x is preferably 0.5 mm or 1 mm or between 0.5 mm and 1 mm. This size has been found to be advantageous since it is large enough to collect a sufficient amount of liquid, but small enough to trap the liquid in the cavity by capillary action, even if the aerosol generating system is rotated or vertically aligned. The dimension x may be chosen depending on the physical properties of the liquid aerosol-forming substrate and need not be equal for the two cavities.

The cavities may also have any suitable length l. For example, the length l of the cavities may be 1 mm, 2 mm, 3 mm, 4 mm, 5 mm or even as much as 1 cm. The length l may be chosen so that the cavities can collect a sufficient amount of liquid. The length l may be chosen depending on the physical properties of the liquid aerosol-forming substrate. The length of the two cavities need not be equal. The cavities may not have the same length l across their entire cross section. For example, the cavities may be asymmetric.

In FIGS. 3 and 4, the cavities 305, 307 are shown positioned at a cross sectional distance a from the exterior of the aerosol generating system. Distance a can be chosen to have any value and may not be equal for the two cavities. Similarly, the cavities 305, 307 are shown positioned at a cross sectional distance b from the air outlet 125 of the aerosol generating system. Distance b can be chosen to have any value and may not be equal for the two cavities. All the dimensions may be chosen as desired, depending on, for example, the desired size for the aerosol generating system and the physical properties of the liquid aerosol-forming substrate.

In FIGS. 3 and 4, the cavities are located close to the air outlet. This may be preferable, because this location has been found to be most effective for collecting the liquid droplets. This is because air flow in the aerosol generating system may have a tendency to push the liquid droplets towards the air outlet. However, the cavities may be located elsewhere in the aerosol-forming chamber. In FIGS. 3 and 4, two cavities are provided, one either side of the air outlet. However, any suitable number of cavities, including a single cavity, may be provided. For example, more than two cavities may be provided and these may be arranged substantially in a circle around, for example concentric with, the air outlet 125. The cavities may be linked to one another. The cavities may also be connected to the capillary wick, for example via one or more return passageways. This will allow the liquid collecting in the cavities to be recycled. Other variations are possible.

Figures 5, 6:
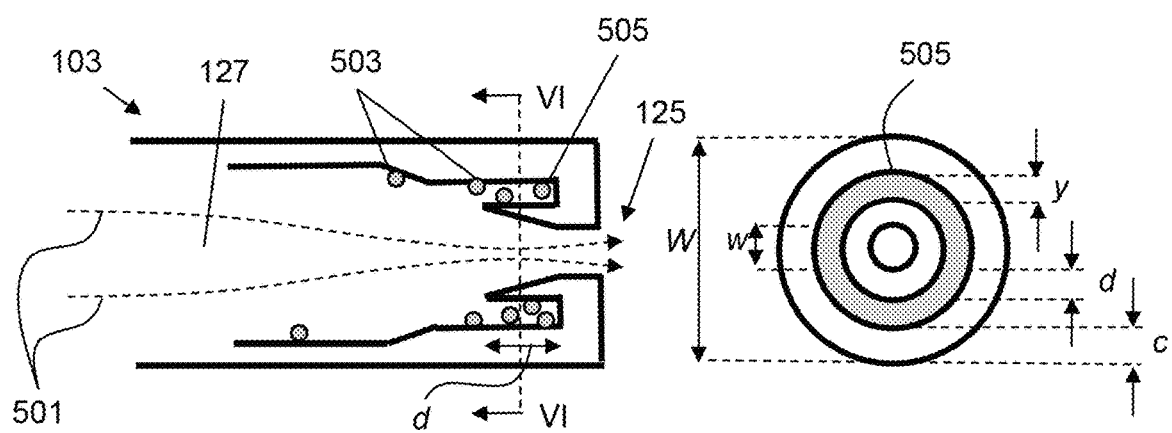
FIG. 5 shows an enlarged view of the mouthpiece end of an alternative aerosol generating system according to the first embodiment of the invention.
FIG. 6 is a cross sectional view along line VI-VI of FIG. 5.
Figure 7:
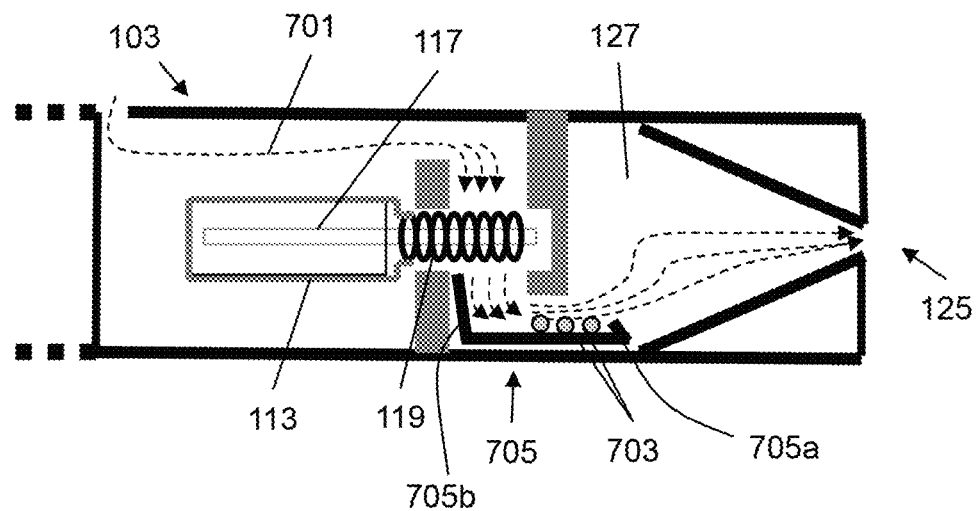
FIG. 7 shows an enlarged view of the mouthpiece end of an aerosol generating system according to a second embodiment of the invention.

FIG. 5 shows an enlarged view of the mouthpiece end of an alternative aerosol generating system according to the first embodiment of the invention. FIG. 6 is a cross sectional view along line VI-VI of FIG. 5. FIG. 5 shows the mouthpiece end 103 including the aerosol-forming chamber 127 and the air outlet 125. Other components are not shown in FIG. 5, for clarity. In FIG. 5, the air flow is shown schematically by arrows 501 and liquid droplets 503 are shown accumulating on the inside walls of the aerosol-forming chamber 127.

In the embodiment shown in FIGS. 5 and 6, the inside walls of the aerosol-forming chamber are provided with a single droplet collecting cavity or recess 505. As seen in FIG. 6, the cavity 505 is in the form of a substantially annular groove surrounding air outlet 125. As with cavities 305 and 307 in FIGS. 3 and 4, the cavity 505 is a blind cavity. That is to say, the cavity 505 does not extend to the outside of the aerosol generating system.

The cavity 505 acts as leakage prevention means. The cavity 505 collects liquid condensate droplets 503 which have accumulated on the inside walls of the aerosol-forming chamber 127. The cavity 505 is positioned so as to interrupt the flow route for liquid droplets 503 running towards the air outlet. Thus, the liquid droplets are prevented from leaking out of the air outlet of the aerosol generating system.

In FIGS. 5 and 6, the cavity is in the form of a circular annular groove. However, the cavity may have any suitable cross section and shape. As in FIGS. 3 and 4, in FIGS. 5 and 6, the cross sectional dimension of the aerosol generating system at the air outlet end is shown as W and the cross sectional dimension of the air outlet itself is shown as w. W and w may have any suitable values as discussed above. For example, W may be between 5 mm and 30 mm and w may be between 1 mm and 5 mm.

In FIGS. 5 and 6, the cavity 505 is shown with an annular cross sectional width y. Width y is the difference between the radius of the outer circle forming the annulus and the radius of the inner circle forming the annulus. Dimension y is preferably 0.5 mm or 1 mm or between 0.5 mm and 1 mm. This size has been found to be advantageous since it is large enough to collect a sufficient amount of liquid, but small enough to trap the liquid in the cavity by capillary action, even if the aerosol generating system is rotated or vertically aligned. The dimension y may be chosen depending on the physical properties of the liquid aerosol-forming substrate.

The cavity may also have any suitable depth d. For example, the depth d of the cavity may be 1 mm, 2 mm, 3 mm, 4 mm, 5 mm or even as much as 1 cm. The depth d may be chosen so that the cavity 505 can collect a sufficient amount of liquid. The depth d may be chosen depending on the physical properties of the liquid aerosol-forming substrate. The cavity may not have the same depth d across the entire cross section.

In FIGS. 5 and 6, the cavity 505 is shown positioned at a cross sectional distance c from the outside of the aerosol generating system. That is to say, the distance from the outer circle forming the annulus and the exterior of the aerosol generating system is c. Distance c can be chosen to have any value. Similarly, the cavity 505 is shown positioned at a cross sectional distance d from the air outlet 125 of the aerosol generating system. Distance d can be chosen to have any value. In FIGS. 5 and 6, the cavity is symmetrically located around the air outlet. However, this need not be the case and the annular cavity may, instead, be off-centre. All the dimensions can be chosen as desired, depending on, for example, the desired size for the aerosol generating system and the physical properties of the liquid aerosol-forming substrate.

In FIGS. 5 and 6, the annular cavity is located close to the air outlet. This may be preferable, because this location has been found to be most effective for collecting the liquid droplets. This is because air flow in the aerosol generating system may have a tendency to push the liquid droplets towards the air outlet. However, the cavity may be located elsewhere in the aerosol-forming chamber. In addition, several concentric grooves may be provided. The cavity may also be connected to the capillary wick, for example via one or more return passageways. This will allow the liquid collecting in the cavities to be recycled. Other variations are possible.

In the embodiments shown in FIGS. 3, 4, 5 and 6, the cavity or cavities may contain capillary material. The cavity or cavities may be substantially filled with capillary material. The capillary material in the cavity is arranged to hold the liquid condensate collecting in the cavity. In that way, the amount of free liquid, that is to say, liquid which is free to flow, is reduced. Providing such capillary material further reduces the likelihood that condensed liquid will leak from the aerosol generating system. The capillary material may extend out of the cavity and connect to the capillary wick. For example, the capillary material may extend through a return passageway. This allows condensed liquid to be recycled.

The capillary material may comprise any material which is suitable for retaining the liquid. Examples of suitable materials are a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Thus, in the embodiments shown in FIGS. 3, 4, 5 and 6, leakage prevention means are provided in the form of one or more liquid collecting cavities. The cavity or cavities allow condensed liquid droplets to be collected, thereby preventing leakage from the aerosol generating system. Optionally, the collected liquid may be recycled back to the capillary wick, thereby reducing wastage.

FIG. 7 shows an enlarged view of the mouthpiece end of an aerosol generating system according to a second embodiment of the invention. FIG. 7 shows the mouthpiece end 103 including the cartridge 113, the capillary wick 117, the heater 119, the aerosol-forming chamber 127 and the air outlet 125. Other components are not shown in FIG. 7 for clarity.

In FIG. 7, air flow is shown schematically by arrows 701. It can be seen that air flow is directed across the capillary wick and heater in a substantially perpendicular direction. That is to say, the air flow is substantially perpendicular to the longitudinal axis of the housing and the capillary wick. In FIG. 7, one inside wall of the housing is provided with a hooked member 705. The hooked member 705 has a hook 705*a* at its end furthest from the capillary wick and a sloped portion 705*b* at its end nearest to the capillary wick. Liquid droplets 703 are shown accumulating on the inside of the hooked member 705 between the capillary wick 117 and heater 119 and the air outlet 125. The hooked member 705 acts as leakage prevention means. The hooked member 705 collects, in the hook 705*a*, condensed liquid droplets which would otherwise collect on the inside walls. The hook 705*a* prevents the liquid droplets from flowing further downstream. The hooked member 705 provides a recycle path in the form of sloped portion 705*b* to channel the collected liquid droplets back to the capillary wick.

In FIG. 7, the air flow is shown directed in a direction substantially perpendicular to the capillary wick and heater. However, the leakage prevention means in the form of hooked member 705 may still be provided when the air flow is not in a direction substantially perpendicular to the capillary wick and heater. The hooked member is, however, particularly effective in the embodiment of FIG. 7 because the air flow direction means that there is a tendency for condensed liquid droplets to form in the region of the hooked member. The hooked member 705 may take any appropriate form. For example, the hooked member may extend around all or part of the circumference of the aerosol generating system. The hooked member may extend along any length of the aerosol generating system between the capillary wick and heater and the air outlet. The hooked member may be provided on a wall of the aerosol-forming chamber. More than one hooked member may be provided.

The sloped portion 705*b* of the hooked member need not be provided. However, the sloped portion 705*b* is advantageous because it assists with transfer of liquid droplets back to the capillary wick. The sloped portion prevents liquid droplets accumulating between the hook and the capillary wick. The sloped portion may have any appropriate angle and length. The hook 705*a* of the hooked member collects the liquid droplets. The hook may have any appropriate shape. The shape of the hook may depend on the size of condensed liquid droplets expected. This may be determined by the physical properties of the liquid aerosol-forming substrate.

In one variation of the embodiment shown in FIG. 7, the hooked member 705 may include capillary material on part or all of its surface. That capillary material is arranged to hold liquid condensate collecting on the hooked member. In that way, the amount of free liquid, that is to say, liquid which is free to flow, is reduced. Providing such capillary material further reduces the likelihood that condensed liquid will leak from the aerosol generating system. The capillary material assists with the transfer of the condensed liquid droplets back to the capillary wick. The capillary material may be in contact with the capillary wick. This allows liquid to be recycled.

The capillary material may comprise any material or combination of materials which is suitable for retaining the liquid. Examples of suitable materials are a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Thus, in the embodiment shown in FIG. 7, leakage prevention means are provided in the form of a hooked member. The hooked member allows liquid droplets to be collected thereby preventing leakage of liquid condensate from the aerosol generating system. Optionally, the collected liquid may be recycled back to the capillary wick, thereby reducing wastage.

Figure 8:
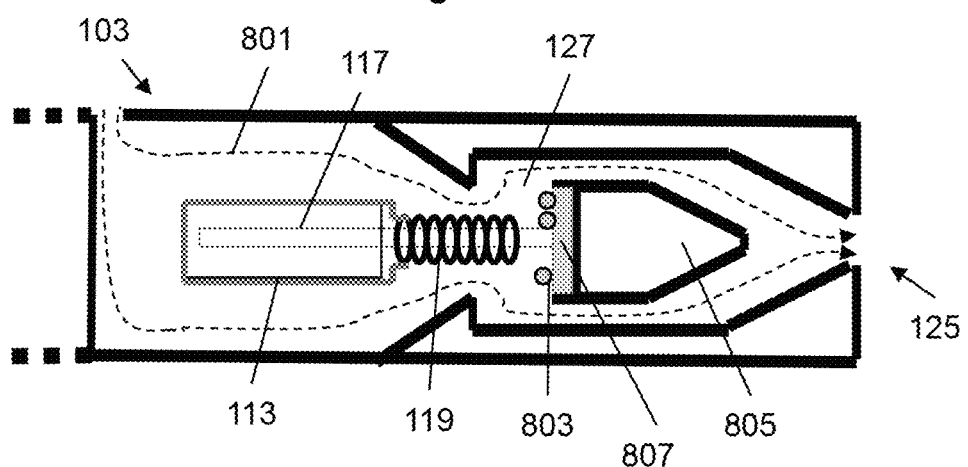
FIG. 8 shows an enlarged view of the mouthpiece end of an aerosol generating system according to a third embodiment of the invention.

FIG. 8 shows an enlarged view of the mouthpiece end of an aerosol generating system according to a third embodiment of the invention. FIG. 8 shows the mouthpiece end 103 including the cartridge 113, the capillary wick 117, the heater 119, the aerosol-forming chamber 127 and the air outlet 125. Other components are not shown in FIG. 8 for clarity. In FIG. 8, air flow is shown schematically by arrows 801.

The aerosol generating system of FIG. 8 further includes an impactor 805 positioned on the downstream side of the capillary wick and heater. The impactor 805 allows liquid droplets 803 to be trapped on the upstream side of the impactor. In FIG. 8, impactor 805 includes capillary material 807 on the upstream side although this need not be included. In FIG. 8, the capillary material 807 is in direct contact with capillary wick 117, although this direct contact is optional. The contact allows any liquid droplets collected by impactor 805 to be transferred back to the capillary wick.

The impactor 805 acts as leakage prevention means. The impactor collects liquid droplets, which may otherwise collect on the inside walls. The impactor disrupts the airflow in the aerosol generating system downstream of the capillary wick and heater. The impactor tends to collect the larger droplets. Larger droplets may be droplets having a diameter greater than around 1.0 µm. Alternatively, larger droplets may be droplets having a diameter greater than around 1.5 µm This is because the larger droplets have the greatest inertia and are therefore most likely to collect on the impactor. Smaller liquid droplets tend to be carried in the air flow diverting around the impactor. But, larger liquid droplets cannot undergo such a diversion around the impactor and the larger droplets impact on the upstream side of the impactor instead.

If the impactor includes capillary material at least on its upstream side, the liquid droplets may be more easily retained. In that way, the amount of free liquid, that is to say, liquid which is free to flow, is reduced. Providing such capillary material further reduces the likelihood that liquid will leak from the aerosol generating system. If the capillary material is in contact with the capillary wick, this allows collected liquid droplets to be transferred back to the capillary wick. This allows liquid to be recycled.

The impactor 805 may take any appropriate form. For example, the impactor may have any suitable cross sectional shape and size. The upstream surface of the impactor, on which capillary material may be located, may have any suitable shape and size. The size of the upstream surface of the impactor will affect the size of liquid droplets which are collected. A small upstream surface area will allow only the largest droplets to be collected. A larger upstream surface area will allow smaller droplets to be collected too. Thus, the size of the upstream surface may be chosen depending on the desired aerosol properties and the physical properties of the liquid aerosol-forming substrate.

If the impactor is provided with capillary material in contact with the capillary wick, the impactor may be positioned at any suitable distance from the heater. The distance from the heater will affect the size of the droplets which are collected on the impactor. If the impactor is not provided with capillary material in contact with the capillary wick, the impactor may be positioned at any suitable distance from the capillary wick and heater. Preferably, the impactor is supported in the aerosol-forming chamber by one or more struts (not shown in FIG. 8).

In FIG. 8, capillary material is shown on the upstream surface of the impactor 805. The capillary material may be provided on all or part of the upstream surface. Capillary material may additionally or alternatively be provided on other surfaces of the impactor. The capillary material may comprise any material or combination of materials which is suitable for retaining the liquid. Examples of suitable materials are a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Thus, in the embodiment shown in FIG. 8, leakage prevention means are provided in the form of an impactor. The impactor disrupts the air flow thereby allowing liquid droplets to be collected. This prevents or at least reduces leakage from the aerosol generating system. Optionally, the collected liquid may be recycled back to the capillary wick, thereby reducing wastage.

Figure 9:
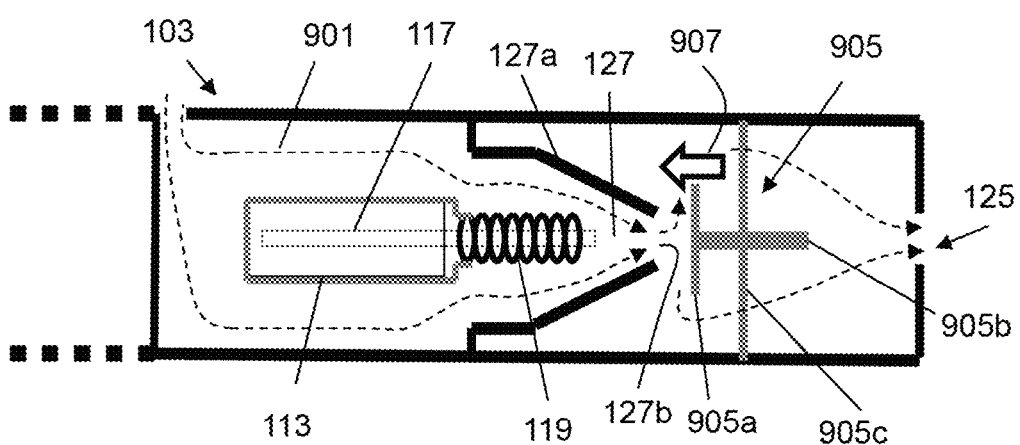
FIG. 9 shows an enlarged view of the mouthpiece end of an aerosol generating system according to a fourth embodiment of the invention.

FIG. 9 shows an enlarged view of the mouthpiece end of an aerosol generating system according to a fourth embodiment of the invention. FIG. 9 shows the mouthpiece end 103 including the cartridge 113, the capillary wick 117, the heater 119, the aerosol-forming chamber 127 and the air outlet 125. In FIG. 9, the aerosol-forming chamber 127 comprise walls 127a and exit 127b. Other components are not shown in FIG. 9 for clarity. In FIG. 9, air flow is shown schematically by arrows 901.

The aerosol generating system of FIG. 9 further includes a closure member 905. In this embodiment, closure member comprises a closure plate 905a supported on a shaft 905b. The closure plate 905a is substantially perpendicular to the longitudinal axis of the system. The shaft 905b is substantially parallel to the longitudinal axis of the system. The shaft 905b is supported inside the aerosol generating system by one or more struts 905c. In FIG. 9, the closure member 905 is shown in the open position. As shown by arrow 907, closure member can be moved towards the aerosol-forming chamber into a closed position.

The closure member 905 acts as leakage prevention means. When the aerosol generating system is in use, the closure member 905 is in the open position (as shown in FIG. 9). An air flow route is provided between the air inlet and the air outlet via the aerosol-forming chamber. The air flows through the aerosol-forming chamber exit 127b and diverts around the closure plate 905a as shown by the arrows 901. When the aerosol generating system is not in use, the closure member 905 may be moved to the closed position (not shown). In the closed position, the closure plate 905a abuts the walls 127a of the aerosol-forming chamber, thereby sealing the aerosol-forming chamber. Any liquid droplets condensing on the inside walls of the aerosol-forming chamber are unable to leak out of the aerosol generating system because the exit 127b is sealed. This is particularly useful, because the aerosol generating system will cool after use and any aerosol remaining in the aerosol-forming chamber will begin to condense into liquid droplets.

The closure member 905 may be manually operated by a user. For example, the shaft 905b may be threaded and may cooperate with a threaded nut (not shown). As the user rotates the closure member in one direction, the closure member will move towards the aerosol-forming chamber and into the closed position. As the user rotates the closure member in the opposite direction, the closure member will move away from the aerosol-forming chamber and into the open position. Thus, the user can set the closure member to the open position before using the aerosol generating system and can set the closure member to the closed position after use.

Alternatively, the closure member 905 may be electrically operated. Again, the shaft 905b may be threaded and may cooperate with a threaded nut (not shown). For example, when the user is about to use the aerosol generating system, the user may move a switch (not shown) into an "on" position. Then, electric circuitry may activate an actuator, for example a motor or an electromagnetic actuator, to move the closure member 905 into the open position. Then, after use, the user can move the switch (not shown) into an "off" position. Then, the electric circuitry may activate the motor to move the closure member into the closed position. Alternatively, the electric circuitry may automatically activate the motor to move the closure member into the closed position. For example, the electric circuitry may be arranged to monitor the time since the last puff. If that time reaches a predetermined threshold, this will indicate that the user has finished using the aerosol generating system. Then, the electric circuitry can activate the motor to move the closure member into the closed position.

The closure member may take any appropriate form. For example, the closure plate may have any suitable surface area as long as it is able to substantially seal the exit of the aerosol-forming chamber. As already mentioned, the shaft 905b may be threaded and may cooperate with a threaded nut. Alternative means for moving the closure member between the closed and open positions may be provided.

The position of the closure member in the open position (as shown in FIG. 9) means that the closure plate 905a may act as an impactor like that shown in FIG. 8. This will depend upon the distance of the closure plate 905a from the capillary wick and heater when the closure member is in the open position. Thus, the closure member 905 may have dual functionality. The closure plate 905a may be provided with capillary material on some or all of its upstream surface. This will allow any liquid droplets which are collected by the closure plate 905a to be retained and will minimise the amount of free liquid. The capillary material may provide a return path for the collected liquid droplets. For example, when the closure member is in the closed position, the capillary material on the plate 905a may contact capillary material on the inside of the walls 127a of the aerosol-forming chamber, thereby allowing liquid to be channeled back towards the capillary wick. The capillary material may comprise any material or combination of materials which is suitable for retaining the liquid. Examples of suitable materials are a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Thus, in the embodiment shown in FIG. 9, leakage prevention means are provided in the form of a closure member. The closure member allows the aerosol-forming chamber to be substantially sealed when the aerosol generating system is not in use. This prevents liquid droplets leaking out of the aerosol generating system. Optionally, any liquid which collects on the closure member may be recycled back to the capillary wick, thereby reducing wastage.

In the above embodiments, capillary material may be provided in conjunction with the leakage prevention means. However, the capillary material may, in fact, be provided alone to act as leakage prevention means in its own right. The capillary material may comprise any material or combination of materials which is suitable for retaining the liquid. Examples of suitable materials are a sponge or foam material, a foamed metal or plastics material, a fibrous material, for example made of spinned or extruded fibres, such as cellulose acetate, polyester, or bonded polyolefin, polyethylene, terylene or polypropylene fibres, nylon fibres or ceramic.

Thus, according to the invention, the aerosol generating system includes leakage prevention means for preventing or reducing leakage of condensed liquid from the aerosol generating system. Embodiments of the leakage prevention means have been described with reference to FIGS. 2 to 9. Features described in relation to one embodiment may also be applicable to another embodiment. For example, the aerosol generating system may be provided with leakage prevention means according to one embodiment as well as leakage prevention means according to another embodiment.

The invention claimed is:

1. An aerosol generating system for heating a liquid aerosol-forming substrate, the system comprising:
    an aerosol-forming chamber; and
    leakage prevention means configured to prevent or reduce leakage of liquid aerosol condensate from the aerosol generating system,
    wherein the leakage prevention means comprises an impactor configured to disrupt airflow in the aerosol-forming chamber so as to collect droplets of liquid being formed from the aerosol-forming substrate having a diameter of greater than 1 micron.

2. The aerosol generating system according to claim 1, wherein the impactor includes capillary material.

3. The aerosol generating system according to claim 1, wherein the leakage prevention means comprises at least one cavity in a wall of the aerosol-forming chamber, configured to collect liquid condensate formed from the aerosol-forming substrate.

4. The aerosol generating system according to claim 3, wherein the at least one cavity contains capillary material.

5. The aerosol generating system according to claim 1, further comprising a liquid storage portion configured to store the liquid aerosol-forming substrate.

6. The aerosol generating system according to claim 1, further comprising a capillary wick configured to convey the liquid aerosol-forming substrate by capillary action.

7. The aerosol generating system according to claim 1, wherein the aerosol generating system is electrically operated and further comprises an electric heater configured to heat the liquid aerosol-forming substrate.

* * * * *